(12) United States Patent
Jin et al.

(10) Patent No.: US 12,115,177 B1
(45) Date of Patent: Oct. 15, 2024

(54) APPLICATION OF PHENYL GLUCURONIDE IN PREPARING DRUG FOR PRE-WARNING OF CANCER VIA INDUCED VOLATOLOMICS

(71) Applicant: Shanghai Jiao Tong University, Shanghai (CN)

(72) Inventors: Han Jin, Shanghai (CN); Daxiang Cui, Shanghai (CN); Cuili Xue, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 0 days.

(21) Appl. No.: 18/518,499

(22) Filed: Nov. 23, 2023

Related U.S. Application Data (63) Continuation of application No. PCT/CN2023/130581, filed on Nov. 9, 2023.

(30) Foreign Application Priority Data

Aug. 15, 2023 (CN) .......................... 202311027767.9

(51) Int. Cl.
*F02M 55/02* (2006.01)
*A61K 31/7034* (2006.01)
*A61K 49/00* (2006.01)

(52) U.S. Cl.
CPC ...... *A61K 31/7034* (2013.01); *A61K 49/0004* (2013.01)

(58) Field of Classification Search
CPC ........................ A61K 31/7034; A61K 49/0004
See application file for complete search history.

(56) References Cited

U.S. PATENT DOCUMENTS

2013/0130292 A1* 5/2013 Szalay ............ G01N 33/56983
435/18

OTHER PUBLICATIONS

Unak et al. "A radioanalytical technique for measurement of beta-glucuronidase activities", Journal of Radioanalytical and Nuclear Chemistry, vol. 266, No. 3 (2005) 503-506 (Year: 2005).*
Li Jilin et al., Application of exhalation analysis in the diagnosis of gastric cancer, Chinese Journal of Difficult and Complicated Cases, Aug. 31, 2018, pp. 856-859, vol. 17, issue 8.
R. I. Russell, C. Watts et al., B-Glucuronidase activity of gastric juice in gastric carcinoma, Gut, 1968, pp. 585-589, vol. 9.
Tadashi Watabe, Kimiko Suzuki et al., The Effect of Various Substituents on the Hydrolysis of Mono-substituted Phenyl-β-D-glucuronic Acids by β-Glucuronidase, Chemical & Pharmaceutical Bulletin, 1970, pp. 414-415, vol. 18, issue 2.
Mattia Marzorati et al., Selective laccase-mediated oxidation of sugars derivatives, Green Chemistry, Jan. 28, 2015, pp. 310-315, vol. 7.
CNIPA, Notification of First Office Action for CN202311027767.9, Jan. 13, 2024.
Shanghai Jiao Tong University (Applicant), Reply to Notification of a First Office Action for CN202311027767.9, w/replacement claims, Feb. 21, 2024.
Shanghai Jiao Tong University (Applicant), Supplemental Reply to Notification of a First Office Action for CN202311027767.9, w/ (allowed) replacement claims, Feb. 28, 2024.
CNIPA, Notification to grant patent right for invention in CN202311027767.9, Mar. 8, 2024.

* cited by examiner

*Primary Examiner* — James W Rogers
(74) *Attorney, Agent, or Firm* — Hemisphere Law, PLLC; Zhigang Ma (57) ABSTRACT

An application phenyl-β-D-glucuronide in preparing a drug for pre-warning of cancer via induced volatolomics is provided, which belongs to the field of cancer detection drugs. Phenyl-β-D-glucuronide exists in natural organisms, which has been verified by animal experiments to be non-toxic and safe. In addition, the phenyl-β-D-glucuronide can be decomposed into phenol which almost does not exist in the body through a tumor part in vivo to serve as a specific marker, so that the influence of individual factors on the pre-warning accuracy in the induced volatolomics can be avoided.

3 Claims, 6 Drawing Sheets

APPLICATION OF PHENYL GLUCURONIDE IN PREPARING DRUG FOR PRE-WARNING OF CANCER VIA INDUCED VOLATOLOMICS

TECHNICAL FIELD

The disclosure relates to the technical field of cancer detection drugs, and more particularly to an application of phenyl-β-D-glucuronide (also referred to as phenyl glucuronide) in preparing a drug for pre-warning of cancer via induced volatolomics (also referred to as induced exhaled breath) method.

BACKGROUND

Cancer is a serious threat to human beings all over the world and an important cause of death. According to the World Health Organization, there are more than 19 million new cancer cases and about 10 million cancer deaths in 2020, which places a heavy physical and economic burden on patients. However, the early clinical symptoms of cancer are not obvious, and the late deterioration progresses rapidly. Therefore, early detection and early treatment of cancer are particularly important for improving the survival rate of cancer. At present, the methods for clinical diagnosis of cancer mainly include computed tomography (CT), magnetic resonance imaging (MRI), ultrasound imaging, positron emission tomography (PET), endoscopy, and examination of cell biological indicators. However, these detection methods are expensive and have a high demand for equipment, which cannot be promoted at the household level and are not conducive to the timely detection of cancer.

Studies have found that there are cancer-related breath markers (i.e., volatile organic compounds (VOCs)) in human exhalation. By comparing the differences in the composition and content of volatile organic compounds in exhalation samples of cancer patients and healthy people, components with significant differences are screened out by technicians as breath biomarkers of cancer and are used for cancer screening. Exhaled breath analysis method has attracted more and more attention due to its advantages of convenient sample collection, non-invasive, and low cost. However, this method of testing by directly collecting patients' exhaled breath belongs to passive breath analysis, and its pre-warning accuracy is greatly affected by individual differences, such as dietary habits, metabolic levels, and regional differences, etc., which can cause fluctuations in the composition of the exhaled breath, resulting in a low pre-warning accuracy, and hardly to meet the requirements of the clinic application. Other studies (e.g., Fabiola Djago, Justin Lange, Pauline Poirot, "Induced volatolomics of pathologies", *Nature Reviews Chemistry*, pages 183-196, Vol. 5, No. 3, 2021) have shown that, through analyzing the presence of specific enzymes that related to the lesion site (tumor) and designing corresponding inducing drugs, pre-warning accuracy of the induced volatolomics way could be greatly improved. In principle, these drugs selectively decompose at the lesion site and produce specific volatile organic compounds as markers. These breath markers induced by drug administration are either absent or present in extremely low concentrations in the original exhaled breath components, thus avoiding the influence of individual differences on breath analysis results.

Therefore, it is necessary to develop an inducing drug suitable for the induced volatolomics based cancer pre-warning.

SUMMARY

In view of the aforementioned issues, the disclosure finds that phenyl-β-D-glucuronide (also referred to as phenyl glucuronide abbreviated as PG) can be decomposed into phenol which can be used as a marker for tumor pre-warning at the lesion site in body, and significant difference in the level of phenol is observed in the breath sample before and after dosing the phenyl-β-D-glucuronide. That is, phenyl-β-D-glucuronide can be applied to the induced volatolomics (also referred to as induced exhaled breath) technology to pre-warn tumors.

In an aspect, the disclosure provides an application of phenyl-β-D-glucuronide in preparing a drug for induced volatolomics based tumor pre-warning.

In another aspect, the disclosure provides a drug for induced volatolomics based tumor pre-warning, including an effective amount of phenyl-β-D-glucuronide and a pharmaceutically acceptable excipient.

The beneficial effects of the disclosure at least include that phenyl-β-D-glucuronide is present in natural plants (soybean metabolites, Ravi Gupta, Cheol Woo Min, et al., "A Multi-Omics Analysis of *Glycine max* Leaves Reveals Alteration in Flavonoid and Isoflavonoid Metabolism Upon Ethylene and Abscisic Acid Treatment", Proteomics, pages 1700366, Vol. 18, No. 7, 2018), and phenyl-β-D-glucuronide has no toxic or side effect and is safe and reliable through animal experiment verification. In addition, phenyl-β-D-glucuronide can be decomposed into phenol, which almost does not exist in vivo, as a specific breath marker through the tumor part in vivo, which can avoid the influence of individual factors on the pre-waring accuracy of induced volatolomics method.

BRIEF DESCRIPTION OF DRAWINGS

FIGS. 1A-1D illustrate stability of drug solutions characterized by ultra-performance liquid chromatography-mass spectrometry (UPLC-MS). Specifically.

FIGS. 2A-2D illustrate stability of the drug solutions characterized by peak distortion analysis (PDA). Specifically.

FIGS. 3A-3E illustrate results of the drug solutions after treatment under different conditions compared with a PDA peak of a phenol standard. Specifically, FIG. 3A illustrates the phenol standard.

DETAILED DESCRIPTION OF EMBODIMENTS

Illustrated embodiments are intended to illustrate the disclosure better, but the content of the disclosure is not intended to limit the illustrated embodiments. Therefore, non-essential modifications and adjustments to the embodiments by those skilled in the art in accordance with the content of the disclosure still fall within the scope of protection of the disclosure.

Terms used herein are only to describe particular embodiments and are not intended to limit the disclosure. Unless it has a significantly different meaning in the context, the singular expression includes expressions in the plural. As used herein, it is understood that terms such as "including", "having", "comprising", and the like are intended to indicate the presence of features, numbers, operations, components, parts, elements, materials, or combinations thereof. The terms of the disclosure are disclosed in the specification and are not intended to exclude the possibility that one or more other features, numbers, operations, components, parts, elements, materials, or combinations thereof may be present or may be added. As used herein, "/" may be interpreted as "and" or "or" depending on circumstances.

The term "effective dose" used in the disclosure refers to a dose of phenyl-β-D-glucuronide that has no physiological toxicity but is sufficient to achieve sufficient production of induced breath biomarkers. The appropriate effective dose in any individual case can be determined by those skilled in the art using routine tests. The effective dose for a specific application scenario will depend on the disease of one or more cancers to be detected, the state of the application object, the route of administration, and other factors known to those in the art. The determination of the effective dose of phenyl-β-D-glucuronide can be completed and optimized by those skilled in the art according to the scheme given by the disclosure.

The term "pharmaceutically acceptable" refers to that reagents used for dissolving drugs meets the requirements in biology or other aspects, that is, the substance can be applied to individuals without causing undesirable biological effects or interacting with any component in the composition containing the substance in a harmful manner. As used in the disclosure, this reagent refers to the reagent familiar to those skilled in the art and acceptable in pharmacy, including water, saline, phosphate buffered saline (PBS) buffer, or glycerol.

An embodiment of the disclosure provides an application of phenyl-β-D-glucuronide in preparing a drug for tumor pre-warning via induced volatolomics (also referred to as induced exhaled breath) method.

It should be understood that phenyl-β-D-glucuronide is a naturally occurring component in soybean, with a molecular formula of $C_{12}H_{14}O_7$, a molecular weight of 270.23, and a CAS accession number of 17685 May 1.

It should be noted that, β-glucuronidase selectively accumulates in the microenvironment of many solid tumors, while in healthy tissues, β-glucuronidase is basically only present in cells, and as a specific enzyme, it can be used for induced volatolomics based tumor pre-warning. Phenyl-β-D-glucuronide is specifically decomposed by β-glucuronidase to produce phenol, and phenyl-β-D-glucuronide has strong hydrophilicity, which limits its passive passage through the cell membrane. Therefore, this decomposition reaction mainly occurs in the tumor microenvironment. In this case, because phenol almost does not exist in the original exhalation of the human body, the phenol marker specifically induced at the tumor site reaches the lungs along with the blood circulation and reaches the exhalation through the gas exchange in the alveoli. Therefore, whether there is a tumor in the body can be judged by detecting the composition and level of phenol in the exhalation. That is to say, it is conducive to timely detection and treatment of cancer in the early stage.

In some specific embodiments, the above tumor may include gastric cancer, colon cancer, intestinal cancer, ovarian cancer, glioma, kidney neoplasms, and lung neoplasms. It should be noted that the above tumors can be all tumors in the body, including benign or malignant tumors, such as gastric cancer, colon cancer, intestinal cancer, ovarian cancer, glioma, kidney neoplasms, or lung neoplasms.

In some specific embodiments, the above drug for induced volatolomics based tumor pre-warning may include an effective amount of phenyl-β-D-glucuronide and a pharmaceutically acceptable excipient. It should be noted that the effective amount of phenyl-β-D-glucuronide is added with the pharmaceutically acceptable excipient to prepare different dosage forms for use, and the dosage form may include any one of a solid dosage form, a liquid dosage form, a paste dosage form, or an aerosol dosage form.

In some specific embodiments, the above pharmaceutically acceptable excipient may include one or more of PBS buffer or physiological saline. It should be noted that the effective amount of phenyl-β-D-glucuronide is added into the PBS buffer or the physiological saline to prepare a liquid dosage form for induced volatolomics based tumor pre-warning. Of course, the PBS buffer or the physiological saline can be replaced by other alternative solutions familiar to those skilled in the art.

Another embodiment of the disclosure provides a drug for induced volatolomics based tumor pre-warning, including an effective amount of phenyl-β-D-glucuronide and a pharmaceutically acceptable excipient. It should be noted that as mentioned above, the effective amount of phenyl-β-D-glucuronide is added with the pharmaceutically acceptable excipient to prepare different dosage forms for use, and the dosage form may include any one of a solid dosage form, a liquid dosage form, a paste dosage form, or an aerosol dosage form. For example, the effective amount of phenyl-β-D-glucuronide is prepared into a liquid dosage form by adding the PBS buffer or the physiological saline.

It should also be noted that phenyl-β-D-glucuronide or the use method of the above drug for induced volatolomics based tumor pre-warning can be completed using active suction devices known in the art.

In order to understand the disclosure better, the content of the disclosure will be further clarified in combination with specific embodiments, but the content of the disclosure is not limited to the following embodiments.

In the following embodiments, phenyl-β-D-glucuronide is purchased from Sigma-Aldrich®, product code: 78555, assay≥99.0% (high performance liquid chromatography abbreviated as HPLC). PBS is purchased from Gibco®. β-glucuronidase is purchased from Sigma-Aldrich®, product code: 8162, quality level 200. Bovine serum albumin is purchased from ChromatoPur, product code: 0218054950.

Dulbecco's modified eagle medium (DMEM), pancreatic enzyme and penicillin-streptomycin (double antibodies) are purchased from Hyclone™. Fetal bovine serum is purchased from Gibco®. MGC-803 cells are obtained from the cell bank of the Chinese Academy of Sciences. Gastric mucosal epithelial cells are obtained from the cell bank of the Chinese Academy of Sciences. Other consumable materials and reagents used are materials commonly used in the art.

Embodiment 1 Stability Verification of Phenyl-β-D-Glucuronide Drug

PBS is used as solvent to prepare a phenyl-β-D-glucuronide solution at a concentration of 400 micrograms per milliliter (μg/mL), 1 mL phenyl-β-D-glucuronide solution is added individually into 1.5-mL injection bottles and sealed. The four bottles of drug solutions are treated as follows: the bottle A is a ready-to-use drug immediately analyzed for composition using ultra performance liquid chromatography mass spectrometry (UPLC-MS); the bottle B is placed in a refrigerator at 4° C. for 2 weeks and then analyzed for composition using UPLC-MS; the bottle C is placed at room temperature (25° C.) for 1 week and then analyzed for composition using UPLC-MS; and the ready-to-use drug in bottle D is analyzed for composition using UPLC-MS and peak distortion analysis (PDA) detectors after heating for 7 hours at 38.5° C. in a water bath. In addition, a 20 parts per million (ppm) phenol standard solution is prepared for UPLC-MS and PDA analysis.

The results are shown in FIGS. 1A-1D, FIGS. 2A-2D, and FIGS. 3A-3E. The HPLC-MS spectrum and the spectral data of PDA detector at 280 nanometers (nm) show that the peaks in the spectra are respectively the effective components in the four bottles of solutions, i.e., the peak areas of phenyl-β-D-glucuronides are the similar (2143, 2142, 2144, and 2160, respectively), and there are no other peaks of the new substances produced (see FIGS. 1A-1D and FIGS. 2A-2D). Compared with the peak of phenol standard, there is no peak of phenol in the four bottles of solutions (see FIGS. 3A-3E).

The above experimental results show that the PBS solution of phenyl-β-D-glucuronide can be stored for at least 1 week at room temperature and at least 2 weeks in a 4° C. refrigerator. The main purpose of setting these three temperatures (i.e., room temperature, 4° C., and 38.5° C.) is to characterize that the drug can be stored in a 4° C. refrigerator or room temperature for a long time without decomposition or deterioration. From the peak area data, it can be seen that the drug can be stored in a 4° C. refrigerator for 2 weeks or at room temperature for 1 week, and the effective component of the drug, phenyl-β-D-glucuronide, is basically unchanged, so under the condition of qualified sealing conditions, the drug solution can be stored for a longer time, which has practical application potential. What's more, within the normal body temperature range (generally less than 38.5° C.), the drug will not decompose by itself without the action of enzymes. The above shows the PBS solution of phenyl-β-D-glucuronide has sufficient stability.

Embodiment 2 In Vitro Enzymatic Reaction of Phenyl-β-D-Glucuronide Drug

A buffer is prepared with sterile water, the main components of the buffer include 75 millimoles per liter (mM) potassium phosphate ($KH_2PO_4$) and 1% bovine serum albumin (BSA), and 1 mole per liter (M) potassium hydroxide (KOH) is used to adjust the pH to 6.8. A phenyl-β-D-glucuronide solution is prepared with deionized water at a concentration of 0.75 grams per liter (g/L). The experiment is divided into a reactive group (also referred to as experimental group) and a control group, and 2.6 mL of deionized water, 2 mL of buffer and 1 mL of phenyl-β-D-glucuronide solution are successively added into two 20 mL injection bottles. After shaking well, they are stabilized in a water bath at 37° C. for 10 minutes. 2 microliters (μL) of β-glucuronidase glycerol solution (enzyme content: 500 U) are added in the bottle of the reactive group, and 2 uL of glycerol is added in the bottle of the control group. The covers are quickly tightened for reacting in a water bath at 37° C. for 1 hour. After the reaction, the aged extraction core is used for headspace solid-phase microextraction (also referred to as solid phase microextraction) for 30 minutes. The gas composition is analyzed by gas chromatography-mass spectrometer (GC-MS), and the extraction core is desorbed at 260° C. for 5 minutes at the sample inlet. The chromatographic column is DB-WAX30 m×0.25 μm×0.25 mm. The temperature rising program is as follows: the initial temperature is 40° C. and kept for 5 minutes, and then the temperature is raised to 250° C. at the rate of 10° C./min and kept for 5 minutes. The full range of the mass spectrometer is scanned from 29 atomic mass units (amu)-400 amu and the carrier gas is high purity helium at a flow rate of 1 milliliter per minute (mL/min), and the detected substances are analyzed using the NIST14 spectral library.

Figure 1A:
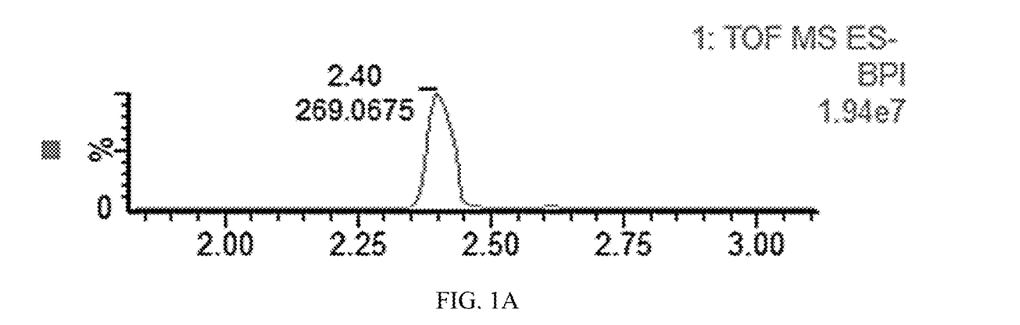
FIG. 1A illustrates a newly prepared drug solution.
Figure 1B:
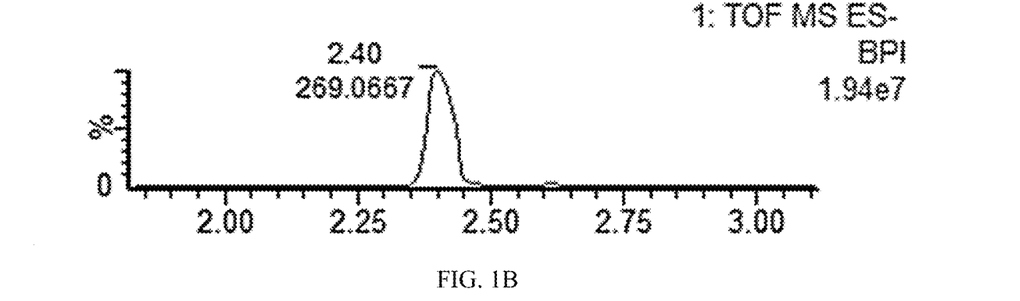
FIG. 1B illustrates a drug solution stored in a refrigerator for two weeks.
Figure 1C:
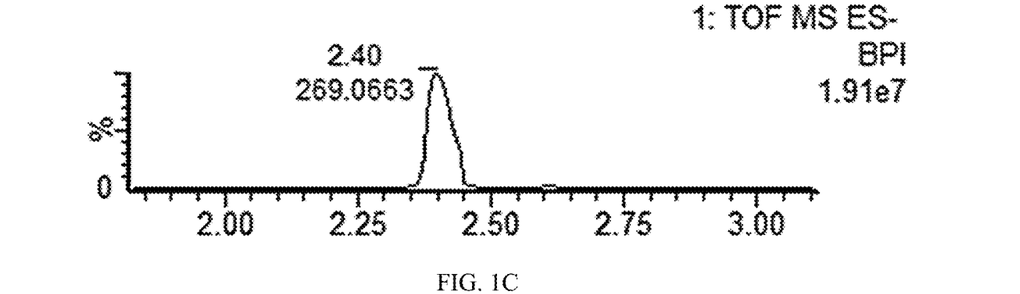
FIG. 1C illustrates a drug solution stored at room temperature for one week.
Figure 1D:
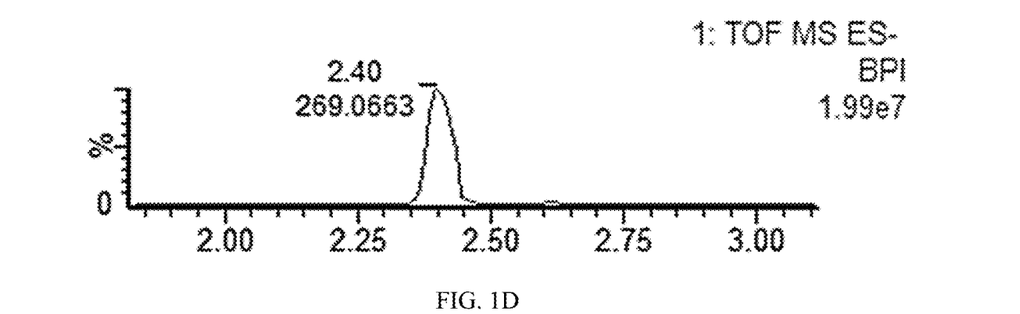
FIG. 1D illustrates a drug solution heated in a 38.5° C. water bath for 7 hours.
Figure 2A:
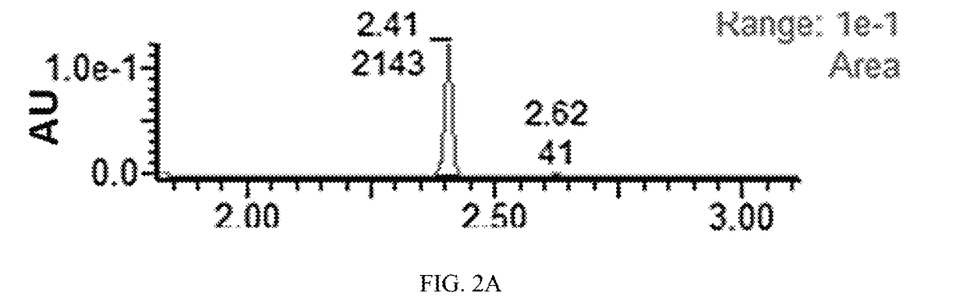
FIG. 2A illustrates the newly prepared drug solution.
Figure 2B:
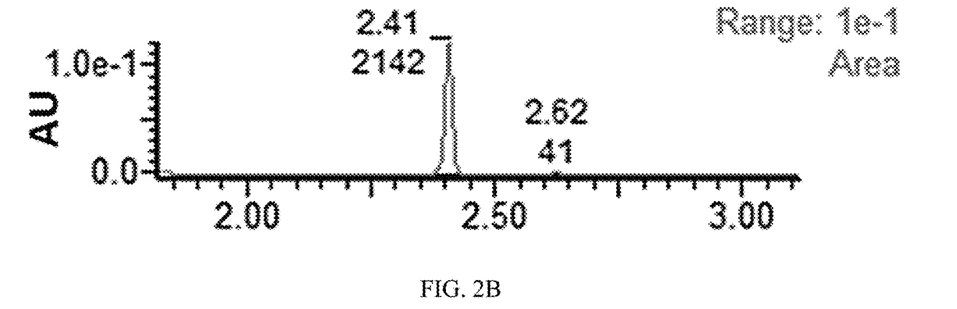
FIG. 2B illustrates the drug solution stored in the refrigerator for two weeks.
Figure 2C:
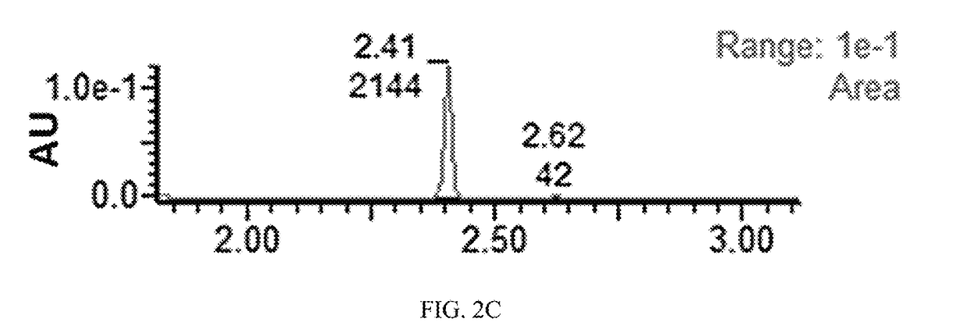
FIG. 2C illustrates the drug solution stored at room temperature for one week.
Figure 2D:
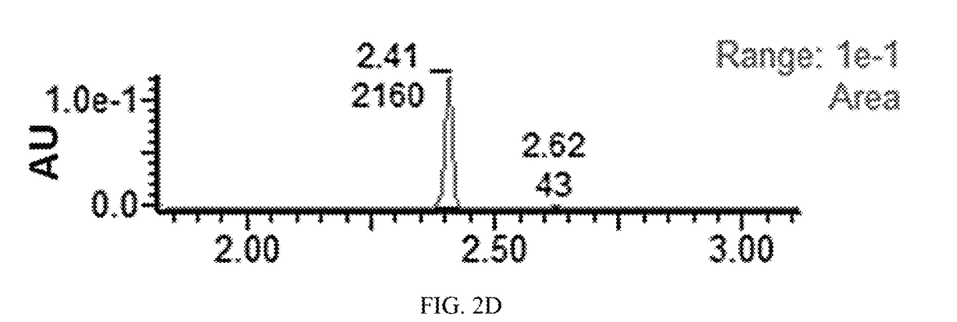
FIG. 2D illustrates the drug solution heated in the 38.5° C. water bath for 7 hours.
Figure 3A:
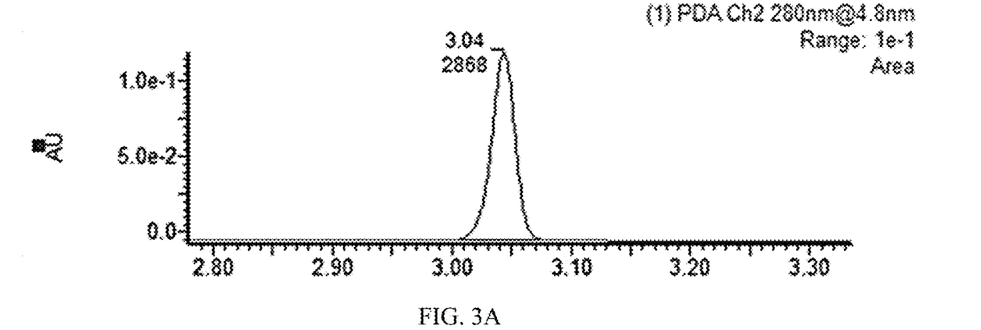
Figure 3B:
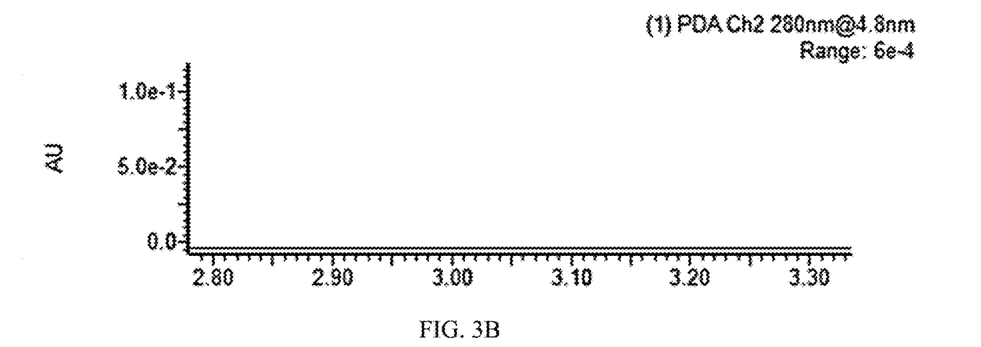
FIG. 3B illustrates the newly prepared drug.
Figure 3C:
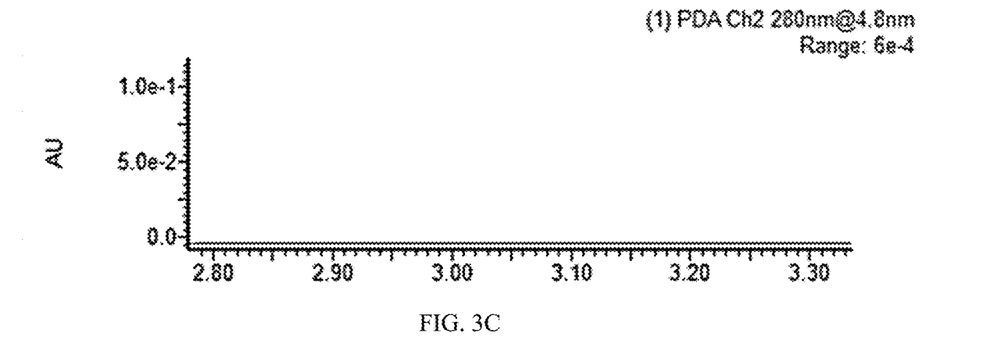
FIG. 3C illustrates the drug solution stored in the refrigerator for two weeks.
Figure 3D:
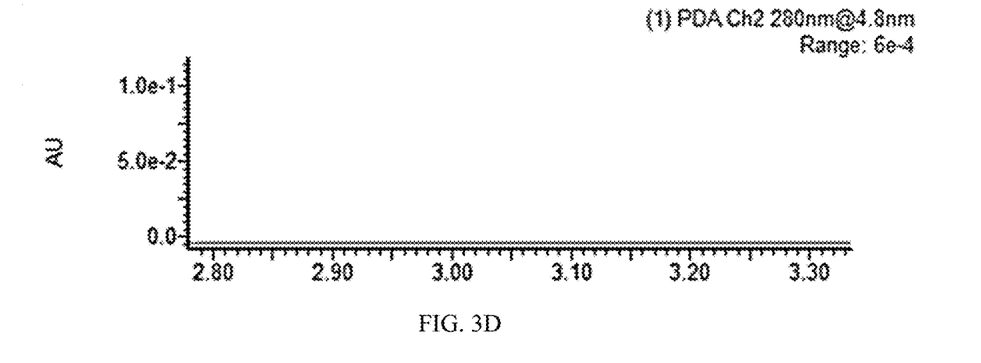
FIG. 3D illustrates the drug solution stored at room temperature for one week.
Figure 3E:
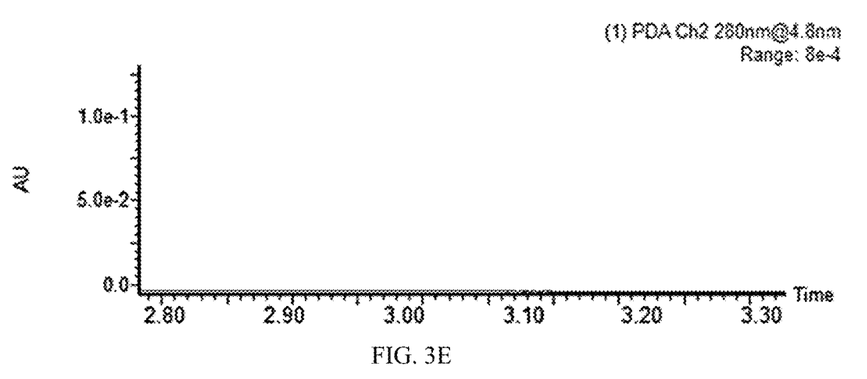
FIG. 3E illustrates the drug solution heated in the 38.5° C. water bath for 7 hours.
Figure 4:
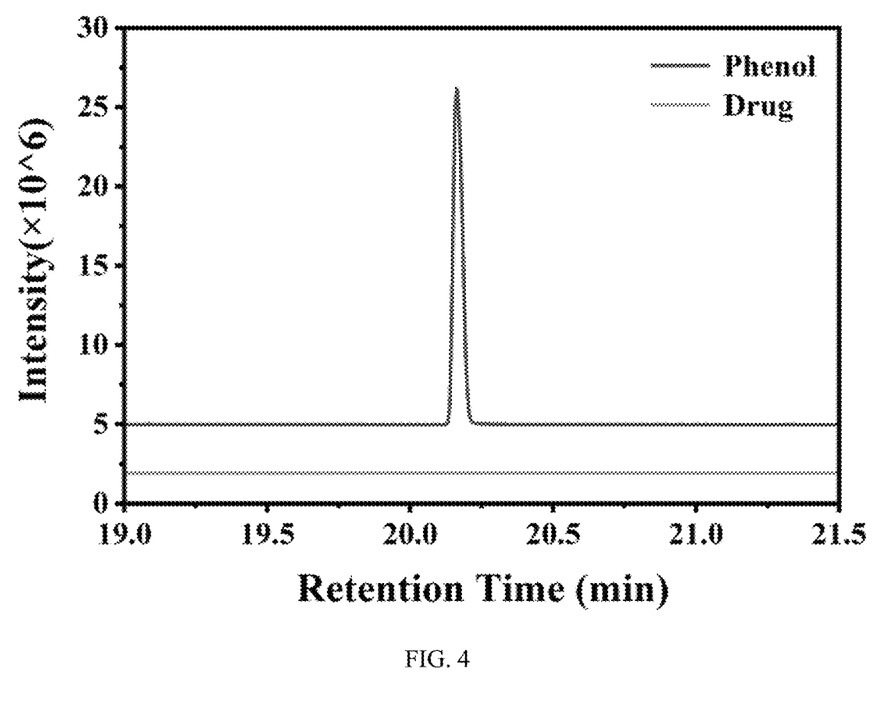
FIG. 4 illustrates that phenol is produced by phenyl-β-D-glucuronide under an action of β-glucuronidase.

As shown in FIG. 4, phenyl-β-D-glucuronide in the experimental group produces phenol under the full action of β-glucuronidase, and is volatilized into the headspace and extracted, while no β-glucuronidase is added in the control group, so the substrate phenyl-β-D-glucuronide is not decomposed and no phenol is produced. The effectiveness of phenyl-β-D-glucuronide as an inducing drug is demonstrated by in vitro enzymatic reaction experiments, which could induce the specific marker. In this situation, the phenol produced in the liquid-phase reaction system can volatilize into the air at room temperature, which also indicates that the specific marker can enter the exhaled breath conditionally through gas exchange in the alveoli.

Embodiment 3 Establishment of Tumor Bearing Mouse Model and Construction of Mouse Exhaled Breath Extraction Device In the embodiment of the disclosure, the mice used are 6-week-old female BALB/c-nude mice, specific pathogen-free (SPF) grade, and the weight at purchase is 17±1.5 g. purchased from Shanghai Jessie Experimental Animal Co., Ltd. Mice are raised in cages in clean animal rooms. The cages are ventilated through a central control system. The indoor temperature is 25±2° C., and the feed and water are used after autoclaved.

After one week of adaptive feeding of the nude mice, the body weight is 20±2 g. During the feeding period, the growth and mental state of the mice are observed every day. The mice are randomly divided into two groups, namely a cancer group and a healthy group. In the cancer group, MGC-803 cells are used to construct a subcutaneous gastric cancer model. Specifically, the complete medium used for culturing the MGC-803 cells includes DMEM high glucose medium, 10% fetal bovine serum, and 1% double antibodies. The MGC-803 cells are resuscitated in 15 mL of complete medium, placed in a 37° C. constant temperature incubator containing 5% carbon dioxide ($CO_2$), and the culture medium is replaced every 2 days. The gastric cancer cells of lepidic growth are digested with pancreatic enzyme, centrifuged, collected, resuspended and counted, dispersed in 15 mL complete medium at a density of $1*10^6$ cells/mL, passed in cell culture flasks and cultured in a cell incubator at a constant temperature. After the cells are adhered to the wall and grown to full size, they are digested with pancreatic enzyme, centrifuged, washed twice with PBS to remove residual serum, resuspended with PBS at a cell density of approximately about $5*10^7$ cells/mL, and a cell inoculation volume of each mouse is 100 µL. The cell suspension used for inoculation should be inoculated within half an hour. During this period, the cells are placed on ice to reduce the metabolic activity of the cells to maintain cell activity. The tumor is implanted in the area with abundant blood supply in the middle and rear of the armpit, and the size of the tumor is measured weekly after the tumor is formed. Generally, the induced volatolomics experiment can be started at the third week after the implantation of the cells.

The exhaled breath extraction device enriches the volatile substances in the exhaled breath of mice to the extraction core of headspace solid-phase microextraction (SPME), which is used to analyze the composition and relative content of the exhaled breath of mice before and after drug administration. A large mouth glass container with a volume of about 400 mL is used, the bottle mouth is frosted, and the sealing gasket, silicone plug and fixing clip are used to ensure sealing. The device is cleaned and dried before use. The mice needed to extract exhaled breath components are put into the glass container. The whole device is placed in a constant temperature environment of 25° C., sealed for 1 hour, and supplemented with oxygen at an interval of 15 minutes by injecting 10 mL of pure oxygen (99.9%) through the silicone plug with a glass syringe. After sealing for 1 hour, a 75 µm Car/PDMS extraction core is inserted into the glass container through the silicone plug, and the black extraction core is extended for headspace solid-phase microextraction for 30 minutes. The extraction process is carried out at a constant temperature of 25° C., and the oxygen is supplemented regularly according to the above process.

The cleanliness and tightness of the device are tested. In the cleanliness test, high-purity nitrogen is introduced into the device, sealed for 1 hour, the gas in the device is absorbed using the SPME extraction core, and the composition of the adsorbed substances is analyzed by gas chromatography-mass spectrometer. Compared with the blank extraction core, it is confirmed that the device itself does not produce impurity gas. After the device is sealed, the syringe is used to inject gas into the device through the silicone plug on the top, and soap water is used for leak detection. There are no bubbles in all parts of the device, and the piston of the syringe can return to its original position after loosening, which proves that the device is well sealed.

Embodiment 4 Phenyl-β-D-Glucuronide for Volatolomics in a Mouse Model of Gastric Cancer The above 10 healthy mice and 10 tumor bearing mice are taken and injected with MGC-803 cells subcutaneously as Day 0 in the experiment. The mice are fed in the cages in the clean animal room. The cages are ventilated through the central control system. The indoor temperature is 25±2° C., and the feed and water are used after autoclaved.

The group of 10 tumor bearing mice and the group of 10 healthy mice are continuously injected with phenyl-β-D-glucuronide drug several times at an interval of 4 days, a single dose (200 µg/kg) of drug is injected intravenously according to the weight of mice each time. The exhaled breath of mice after administration is collected by the above-mentioned mouse exhaled breath extraction device, and the exhaled breath components of mice are collected by the above-mentioned mouse exhaled breath extraction device. The enriched gas components are separated and detected by gas chromatography-mass spectrometer (GCMS): the extraction core is desorbed at 260° C. for 5 minutes at the sample inlet; and the chromatographic column is DB-WAX30 m×0.25 µm×0.25 mm. The temperature rising program is as follows: the initial temperature is 40° C. and kept for 5 minutes, and then the temperature is raised to 250° C. at the rate of 10° C./min and kept for 5 minutes. The full range of the mass spectrometer is scanned from 29 amu-400 amu and the carrier gas is high purity helium at a flow rate of 1 mL/min, and the detected substances are analyzed using the NIST14 spectral library.

Figure 5:
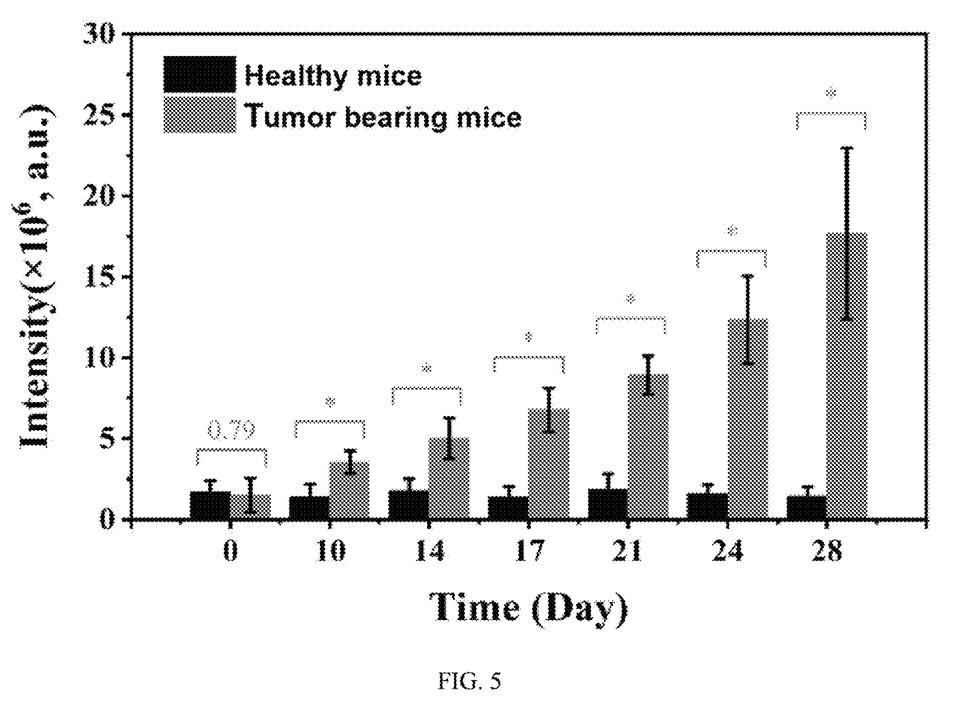
FIG. 5 illustrates production of phenol after phenyl-β-D-glucuronide is administered to a gastric cancer mouse model (i.e., tumor bearing mice) and healthy mice.

At Day 0, since the tumor cells are just injected subcutaneously, there are no solid tumors in vivo in the group of tumor bearing mice, a Mann-Whitney U-test for independent samples is used on the data of the two groups (healthy mice and mice with solid tumors injected with 200 µg/kg drug), and the results are shown in FIG. 5. The results show that the phenol level in the exhaled breath of the tumor bearing mouse group and the healthy mouse group is consistent without significant difference. From the $10^{th}$ day onwards, solid tumors are formed in the tumor bearing mouse group, with a volume of about 100 (cubic millimeters abbreviated as $mm^3$). In each subsequent induced volatolomics, the phenol level in the exhaled breath of the tumor bearing mouse group is significantly higher than that of the healthy group ($p<0.01$), indicating that the induced exhaled breath analysis technology developed in this project can better distinguish mice with gastric cancer and healthy mice.

Figure 6:
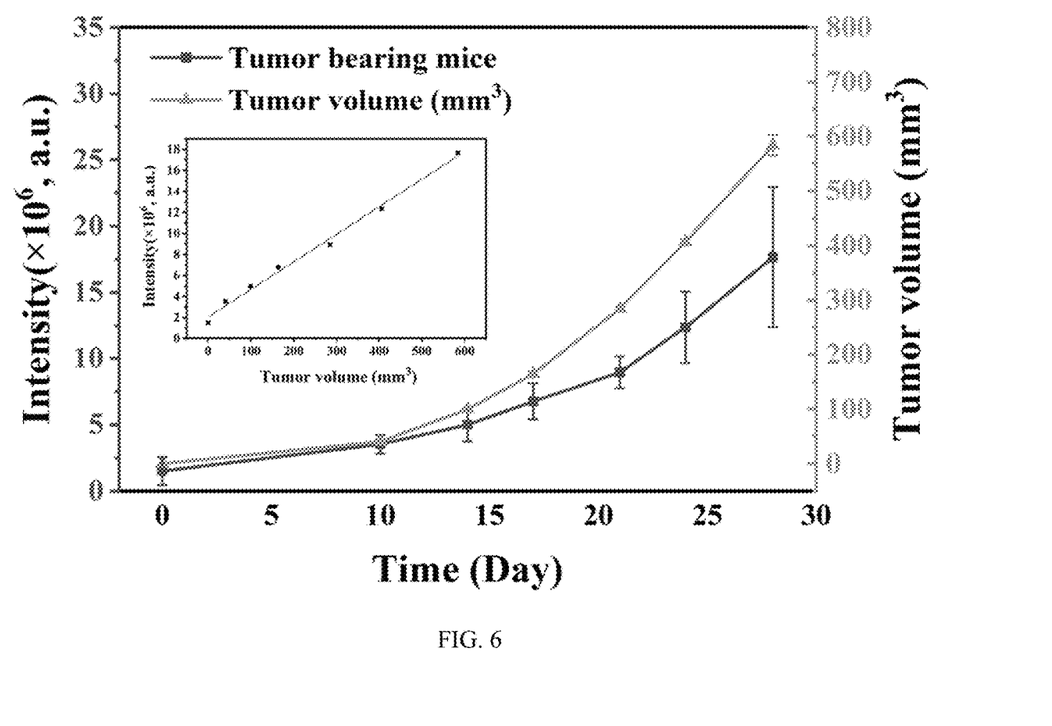
FIG. 6 illustrates a change of phenol level in exhaled breath with tumor volume after administration.

In this situation, it can also be seen from FIG. 6 that the phenol level in the exhaled breath of mice in the tumor bearing mouse group is consistent with the change trend of tumor volume over time. As shown in the illustration of FIG. 6, it is the fitting curve of phenol level in exhaled breath of mice with the change of tumor volume, and the correlation coefficient $R^2$ is 0.993, that is, the phenol level in induced exhaled breath has a good linear correlation with tumor volume, which indicates that the induced exhaled breath diagnostic technology developed in this project can not only be used to screen whether there are solid tumors in the body, but also assist in judging the size of tumors in the body by detecting the phenol level in the exhaled breath. The fitted curve is represented as:

$$\text{tumor volume} = A + B * \text{phenol level in exhaled breath,}$$

where $A=2065116.64068\pm293370.09484$, $B=26167.51388\pm981.43159$.

Therefore, by detecting the content of phenol in exhaled breath, whether there is tumor in mice can be judged and the tumor volume can be estimated, which is expected to achieve early tumor screening and monitoring in the treatment process in clinic.

Embodiment 5 Cytotoxicity Experiment of Phenyl-β-D-Glucuronide

The complete medium used for culturing gastric mucosal epithelial cells includes DMEM high glucose medium, 10% fetal bovine serum, and 1% double antibodies. The gastric mucosal epithelial cells are resuscitated in 15 mL of complete medium, placed in a 37° C. constant temperature incubator containing 5% $CO_2$, and the medium is replaced every 1-2 days. The cultured gastric mucosal epithelial cells are inoculated a 96-well plate with the concentration of $5*10^4$ cells/mL, 100 µL per well, and 5 replicate wells are set up for each group of samples. After 30 hours of cell culture, the culture medium is discarded, the DMEM medium containing phenyl-β-D-glucuronide is added, and the drug concentrations are set at 0 μg/mL, 0.1 μg/mL, 1 μg/mL, 10 μg/mL, 100 μg/mL and 500 μg/mL respectively. There is culture medium without inoculation of the cells with 100 μL per well. After incubation for 40 hours, the culture medium is discarded, 100 μL DMEM medium containing 10% cell counting kit 8 (CCK-8) is added to each well, and then incubated in the incubator for 2 hours. The value of optical density (OD) at 450 nm is monitored with a microplate reader for each well, and the cell viability is calculated based on the value of optical density.

Figure 7:
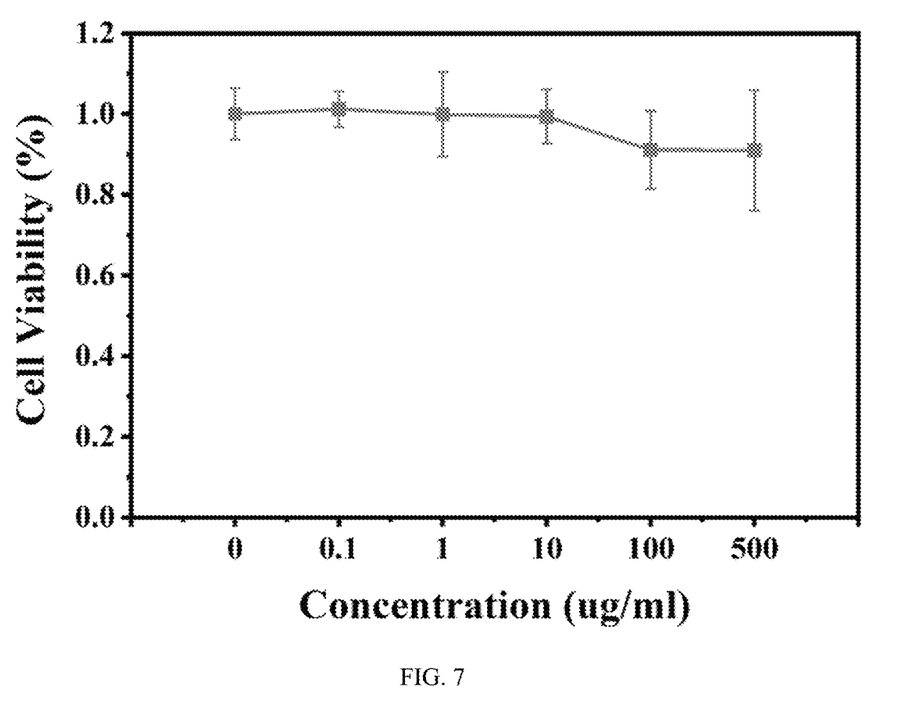
FIG. 7 illustrates effects of different drug concentrations on cell viability characterized by a cell counting kit 8 (CCK-8).

As shown in FIG. 7, in the CCK-8 toxicity experiment on the gastric mucosal epithelial cells, the use of phenyl-β-D-glucuronide at concentrations ranging from 0 to 500 μg/mL has no significant effect on cell viability. Even when the cells are co-cultured with the drug at concentrations as high as 500 μg/mL, the cell viability is still greater than 90%, and the cell viability of gastric mucosal epithelial cells is more than 99.3% at the administered concentration of 10 μg/mL. In the actual induced exhaled breath experiment of mice, the administered concentration is 200 μg/kg, and the dosage of each mouse is about 4 μg, which is much lower than the safe concentration value in the CCK-8 experiment, indicating that within the concentration range in the experiment, phenyl-β-D-glucuronide has no toxic effect on cells.

Finally, the above embodiments are only used to illustrate the technical solutions of the disclosure rather than limit them. Although the disclosure is described in detail with reference to the illustrated embodiments, those skilled in the art should understand that modifications or equivalent substitutions can be made to the technical solutions of the disclosure without departing from the purpose and scope of the technical solutions of the disclosure, which should all be covered by the scope of claims of the disclosure.

What is claimed is:

1. An application of a phenyl-β-D-glucuronide drug, comprising:
    applying the phenyl-β-D-glucuronide drug to a subject with a single dose of 200 micrograms per kilogram (μg/kg) body weight of the phenyl-β-D-glucuronide drug via intravenous administration;
    collecting exhaled breath of the subject after the intravenous administration; and
    detecting the exhaled breath of the subject and then analyzing a phenol level of the exhaled breath, to thereby determine whether the subject is a subject bore with a tumor, so as to pre-warn the tumor via induced volatolomics; and
    wherein the tumor is gastric cancer.

2. The application according to claim 1, wherein the phenyl-β-D-glucuronide drug comprises a pharmaceutically acceptable excipient;
    wherein the pharmaceutically acceptable excipient comprises at least one of a phosphate buffered saline (PBS) buffer and a physiological saline.

3. The application according to claim 1, wherein the detecting the exhaled breath of the subject and then analyzing a phenol level of the exhaled breath comprises:
    detecting the exhaled breath of the subject by gas chromatography-mass spectrometer (GCMS) to obtain detected substances; and then analyzing the phenol level in the detected substances of the exhaled breath.

* * * * *